United States Patent [19]

Lee, Jr. et al.

[11] 4,107,845

[45] Aug. 22, 1978

[54] DENTAL ADHESIVE COMPOSITES

[75] Inventors: Henry L. Lee, Jr., Pasadena; Jan Alexander Orlowski, Altadena, both of Calif.

[73] Assignee: Lee Pharmaceuticals, South El Monte, Calif.

[21] Appl. No.: 751,517

[22] Filed: Dec. 16, 1976

Related U.S. Application Data

[63] Continuation of Ser. No. 424,223, Dec. 13, 1973, abandoned, which is a continuation of Ser. No. 215,112, Jan. 3, 1972, abandoned.

[51] Int. Cl.$^2$ ................................................ C08K 7/02
[52] U.S. Cl. ................................ 32/15; 260/42.17; 260/42.28; 260/42.52; 260/998.11
[58] Field of Search ............ 260/42.17, 42.52, 998.11, 260/42.28; 32/15

[56] References Cited

U.S. PATENT DOCUMENTS

| | | | |
|---|---|---|---|
| 3,066,112 | 11/1962 | Bowen | 260/42.15 |
| 3,503,128 | 3/1970 | Boyd | 106/35 |
| 3,539,533 | 11/1970 | Lee et al. | 260/47 |

OTHER PUBLICATIONS

Modern Plastics Encyclopedia 1967, Sep. 1966, vol. 44, vol. A, pp. 599-602, 611-612 & 614.

*Primary Examiner*—James H. Derrington
*Attorney, Agent, or Firm*—Irons and Sears

[57] ABSTRACT

Adhesive dental restorative composite comprising a suspension of filler fibers in a liquid polyacrylate resin composition wherein the resin has a viscosity of less than 5000 centipoise. The fibers which may be organic or inorganic generally have lengths of 1 to 100 microns and diameters which are from 1/20 to 1/5 of the lengths. An amine accelerator and a peroxide catalyst for the acrylate resin are included in the composite. The fibers comprise from 30% to 70% by weight of the composite.

The referred resin formulation comprises from 25% to 90% by weight of a polyethyleneglycol diacrylate and from 10% to 75% by weight of an aromatic or alicyclic polyacrylate compound.

An especially preferred composite is one wherein the resin comprises 40 parts triethyleneglycol dimethacrylate to 60 parts bisphenol-A-bis(3-methacrylato-2-hyroxypropyl) ether having suspended therein calcium silicate fibers having an average length of 5.5 microns, and in which 97% by weight of the fibers have a length less than 20 microns, and 94% a length less than 10 microns. The calcium silicate fibers comprise 55% by weight of the composite.

The composite is particularly useful as a restorative for areas of erosion on teeth, especially gingival erosion in enamel.

26 Claims, No Drawings

DENTAL ADHESIVE COMPOSITES

This application is a continuation of our earlier patent application Ser. No. 424,223, filed Dec. 13, 1973, now abandoned, which in turn was a continuation of our earlier patent application, now abandoned, Ser. No. 215,112, filed Jan. 3, 1972, now abandoned.

BACKGROUND OF THE INVENTION

1. Field of the Invention

This invention is concerned with adhesive dental restorative composites comprised of thermosetting aromatic and alicyclic polyacrylic resins and inorganic and organic filler materials. Because of their adhesiveness, such restoratives do not require normal cavity preparation and are employed without odontomy procedures.

2. Description of the Prior Art

Diacrylate esters of bisphenolic compounds have been used in the prior dental art for direct filling materials when used in combination with a variety of fillers, and have been used without fillers in the prior art for the sealing of developmental defects.

These resins may contain, as a lesser ingredient in the formulation, either methacrylic acid or short-chain aliphatic diacrylates as reactive diluents. The reactive diluents are frequently added to the basic formulation in order to increase the loading volume of inorganic reinforcing fillers or to facilitate penetration of unfilled systems into developmental defects.

In the formulation of these direct filling materials, the amount of filler employed is critical to satisfactory clinical performance. The fillers are employed at loading volumes of from 70–85%, and serve, by their presence to reduce polymerization shrinkage and thermal expansion rates, such reductions being essential to satisfactory retention of the composites in conventional retentive cavity preparations.

The high concentration of fillers conventionally employed provides satisfactory composites for use in conventional retentive cavity preparations, but because of the paste-like consistency of such composites, they possess poor flow characteristics and tend to consolidate prepared enamel and dentin surfaces less well than the unfilled systems. In addition, the poor flow properties make the attainment of smooth, regular junctions between composites and dentin or enamel difficult, generally requiring substantial cutting and finishing with dental instruments after the composite has cured.

Restorative systems based on unfilled polymethylmethacrylate, while having good flow characteristics, and good consolidation of enamel and regular junctions, must be applied with time-consuming techniques for optimal results in order to minimize polymerization shrinkage. Where polymerized beads of methyl methacrylate were used as filler, such compositions did not flow or wet well. Because neither the composites nor unfilled polymethylmethacrylates of the prior art were particularly suited to the requirements of certain nonoperative restorative procedures, conventional cavity preparations continued to be used.

In the prior art, use of more-or-less lightly filled diacrylates or polymethylmethacrylate systems has been avoided because of the resultant sacrifice of strength properties. Furthermore such lightly filled systems were subject to the filler settling during shipment and storage in the dental office. The resuspension of the fillers was excessively difficult and time consuming. Further, the presence of the fillers prevented the realization of proper flow properties, interfered with wetting and the surface consolidation of prepared tooth structure necessary to prolonged retention in the oral environment.

In the prior art, rods, fibers, and whiskers, primarily but not exclusively of glass, have been employed only in blend with particulate and/or spherical fillers. Apparently the very high loading weights required for composites employed in conventional cavity preparations could not be conveniently achieved with primarily fibrous reinforcement since the viscosity tended to increase out of proportion to the loading weights of fibers employed. Thus the highest strengths in clinically practical systems were attainable only with a combination of fillers rather than with the use of exclusively fibrous reinforcement.

A number of systems have been shown to provide enhanced adhesion to dentin and enamel, but the adhesion is progressively lost with time under the wet conditions in the oral environment. Some of the best reported values have been obtained with special polyurethane systems apparently due to the isocyanate component of the formulation scavenging surface water, which would otherwise adversely influence chemical bonding. Improved bonds have also been achieved with special catalysts for acrylic resins, which likewise react with surface water. It has been demonstrated that greater penetration has been achieved with unfilled polymethylmethacrylate than with the filled composite restoratives. Greater surface consolidation of the enamel and dentin is evidenced by tag-like extensions of the resin into the interstices created by the etchant employed in preparing the surface. Such extensions are not readily disrupted by moisture as chemical bonds are quite often.

SUMMARY OF THE INVENTION

According to the present invention there is provided a new adhesive dental composite based upon particular sized filler fibers, or "whiskers," which are suspended in liquid polyacrylate resin blends having viscosities of less than 5,000 centipoise. The particular fibers utilized comprise from 30% to 70% by weight of the total composite. The composites of the present invention are unusually adhesive to etched enamel and dentin.

Utilizing the composites of the present invention, developmental enamel defects, hypocalcified lesions, and eroded or abraded enamel or dentin may be repaired, without the need for conventional cavity preparations and the resultant sacrifice of sound tooth structure. Additionally, when properly formulated, these new composites may be used without operative procedures for coating stained enamel and for masking other restorative materials, such as unsightly amalgam fillings.

It has been found that the difficulties encountered in the prior art may be overcome by the use of special fibrous reinforcement in thermosetting diacrylate resins having a viscosity of less than 5,000 centipoise. Excellent suspensions may be achieved with such diacrylate resins or blends. Most surprisingly, when the particular fillers are used at the specified loading weights, they impart improved strength properties, especially high compressive strengths, as well as hardness and edge strengths. When the fiber fillers are employed at loading weights to achieve these desirable properties, the adhesive composites exhibit excellent flow characteristics which account in part for the outstanding consolidation of the prepared dentin or enamel surfaces.

The adhesive dental restorative composites of this invention have a unique combination of strength, relatively low polymerization shrinkage, excellent stability in storage, particularly in maintaining the filler in suspension, excellent flowability, excellent wetability of enamel and dentin, and outstanding adhesiveness which is not subject to objectionable degradation when exposed to water in the oral environment.

The adhesive composites of the present invention exhibit tag-like extensions similar to those obtained with unfilled polymethyl methacrylate. It is theorized that the fibrous reinforcements, at the loading weights employed, do not block the interstices of enamel and dentin to as great a degree as do particulate fillers at the same loading weights. Also the diacrylate systems used in the composites of this invention, saturate and fill the interstices readily. The net effect of this surface consolidation is to provide higher orders of mechanical interlocking and hence higher measured adhesive strengths than are experienced with the composites of the prior art. Some of the fibers are so oriented during application that they penetrate to some extent into the prepared enamel or dentinal defects to serve as additional mechanical support against shear forces to improve the overall structural integrity of the interlock between the cured composite and the substrate.

Such mechanical adhesion is less subject to disruption in the oral environment than are chemical bonds established between the enamel and dentin and the composite material. The adhesive strength obtained is less dependent on the specific chemical nature of the surface which may include the presence of absorbed monolayers of water and the presence of fluoridated species.

The fibers or whiskers which are employed as the filler in the adhesive composite of this invention are from 1 to 100 microns in length and have diameters which on the average are from 1/20 to 1/5 the lengths of the fibers. In general, any fibrous material, organic or inorganic, of the appropriate dimensions is suitable for reinforcing the diacrylate matrix, provided only that reinforcing material provides acceptable aesthetics to the cured composite. Within these broad limits, some materials are preferable to others. For example, while quartz rods and fibers may be used, we have found it more advantageous to use fibers having a hardness on the Mohs scale of from about 3.5 to about 6, such fibers imparting improved polishability to the cured composite over the harder fibers. While sapphire fibers may be used, these are inherently expensive and are less desirable than less expensive fibers, such as calcium silicate fibers. Organic fibers are inherently expensive to obtain in the required form, and while offering acceptable aesthetics and improved polishability, they do not offer equivalent reduction in thermal expansion rates to the cured composite as offered by the inorganic fibers, and are generally more soluble in the oral fluids than are the inorganic fibers. In general then, inorganic fibers are preferred, and we have found that calcium silicate fibers are particularly suited. The term fiber as used herein includes materials commonly termed fibers, rods, or whiskers, provided they have the indicated dimensions.

The particular degree of fiber loading of the composite will depend on the original viscosity of the resin composition employed and the particular final flow properties desired. With resins of low initial viscosity, higher loading weights of fibers may be employed, and conversely, with resins of higher initial viscosities, lower loading weights of fibers are utilized. In general, the exact loading weight is determined by the flow properties of the final composite and should be such that tag-like extensions into etched enamel are at least 20 microns long.

An accelerator and a catalyst for the resin are included in the composite formulations in amounts to give convenient gel and set times. Gel times of 1 to 2 minutes, and set times of 1 to 5 minutes are generally suitable. Amine accelerators and peroxide catalysts are preferred.

As indicated, the adhesive dental restorative composites of this invention make it possible to repair eroded enamel and dentin, especially in the case of gingival erosion, without the necessity of time consuming classical operative preparations. It is only necessary to pretreat the enamel or dentin with a suitable etchant such as an inorganic acid like phosphoric or hydrochloric acid, or an organic acid such as citric acid. The etchant serves to remove plaque and oral debris and to condition the substrate to make it more receptive to wetting and receiving the tag-like extensions of the adhesive composite.

It is very important that the surface to be treated be thoroughly dried prior to application of the adhesive composites of this invention.

While not essential to the successful application of the adhesive composite of this invention, greater adhesive strength is obtained if following the etchant application, the tooth is treated with a keying agent. It is also recommended that the filler fibers be treated with a keying agent prior to incorporation into the composite. Such keying agents are known to the art and include among others organofunctional silanes. We have found that particularly good results are obtained if the tooth is treated with a silane wherein the organofunctional group is epoxy. Preferably the silane agent for treating the fiber has an acrylic functional group.

DESCRIPTION OF THE PREFERRED EMBODIMENTS

As indicated, the adhesive restorative composite of this invention comprises a suspension of fiber filler, wherein the fibers are from 1 to 100 microns in length and have diameters which on the average are from 1/20 to 1/5 the length of the fibers, in a diacrylate resin or resin blend which has an initial viscosity of less than 5,000 centipoise, and in which the fibers comprise from 30% to 70% by weight of the composite. Preferably the fibers comprise from 40% to 70% by weight, with about 55% most preferred.

While in general any organic or inorganic filler fiber having the above dimensions may be utilized, inorganic fibers having a hardness on the Mohs scale of 3.5 to 6.0 are preferred as mentioned above. Particularly preferred are calcium silicate fibers. One commercially available blend of calcium silicate fiber that is very satisfactory has an average fiber length of 5.5 microns, with 97% by weight of the fibers being less than 20 microns in length and 94% by weight less than 10 microns in length, with diameters on the average of 1/15 to 1/13 the lengths.

The resin component of the composite of this invention preferably comprises a blend of from 25% to 90% by weight of a compound of the formula:

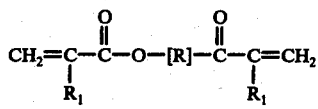

I wherein
R$_1$ is hydrogen or alkyl of 1 to 4 carbons, hydrogen or methyl being preferred, and methyl most preferred;
R is:

a) 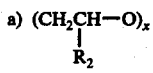

wherein x is an integer of 1 to 5, preferably 3, and R$_2$ is hydrogen or alkyl of 1 to 4 carbon atoms, hydrogen being preferred;

(b) CH$_2$(CH$_2$)$_y$CH$_2$O wherein y is an integer of 1 or 2;

c) 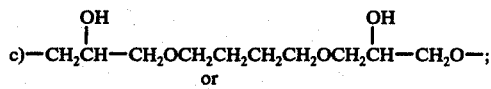
or d) 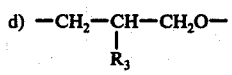

wherein R$_3$ is OH or

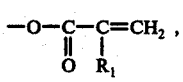

and R$_1$ has the same meaning as above, with from 10% to 75%, preferably 30% to 70%, by weight of an aromatic or alicyclic polyacrylate compound, provided the viscosity of the blend is less than 5,000 centipoise. The preferred resin blends have excellent handling characteristics, very satisfactory gel and set times, high compressive and flexural strengths, low degree of shrinkage on cure, and low coefficients of thermal expansion. In addition, they have relatively low water adsorption. Especially preferred among the compounds of Formula I are dimethacrylates under a) above and in particular triethyleneglycol dimethacrylate.

It is preferred that the aromatic polyacrylate contain at least 2 aromatic rings in its structure and likewise that the alicyclic polyacrylate contain at least 2 alicyclic rings in its structure. Among the preferred members of the diaromatic polyacrylates is BIS-GMA or bisphenol-A-bis (3-methacrylato-2-hydroxypropyl)ether, or the dimethacrylate derived from the ethylene or propylene oxide adduct of bisphenol-A.

A preferred dialicyclic is the dimethacrylate derived from hydrogenated bisphenol.

The most preferred component in the blend with the compounds of Formula I is bisphenol-A-bis(3-methacrylato-2-hydroxypropyl) ether.

A particularly preferred composite according to this invention comprises a suspension of calcium silicate fibers in a resin blend of about 60 parts by weight bisphenol-A-bis(3-methacrylato-2-hydroxypropyl) ether and 40 parts by weight triethyleneglycol dimethacrylate, wherein the fibers comprise about 55% by weight of the composite.

Representative of aromatic and alicyclic polyacrylates which are utilized in the practice of this invention, besides those mentioned above, are compounds such as:

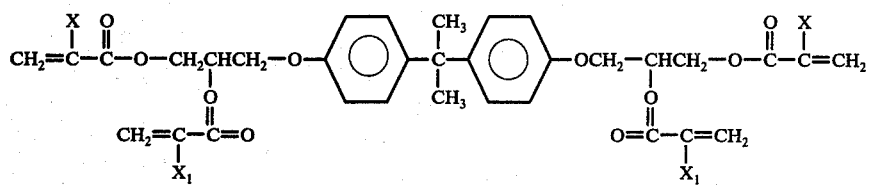

II wherein each of X and X$_1$ may independently be hydrogen, lower alkyl, i.e., straight or branched chain alkyl of 1 to 4 carbon atoms, methyl being preferred, or halogen, chlorine being preferred. A preferred example of a compound of Formula II is:

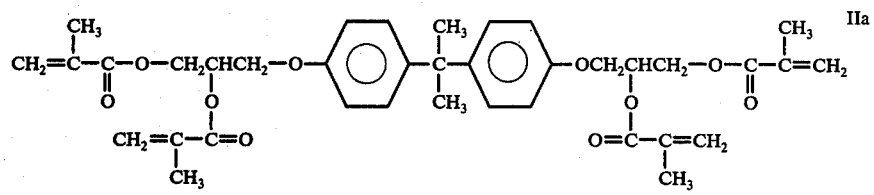

IIa which may be named bisphenol-A-bis(2,3-dimethacrylatopropyl ester);

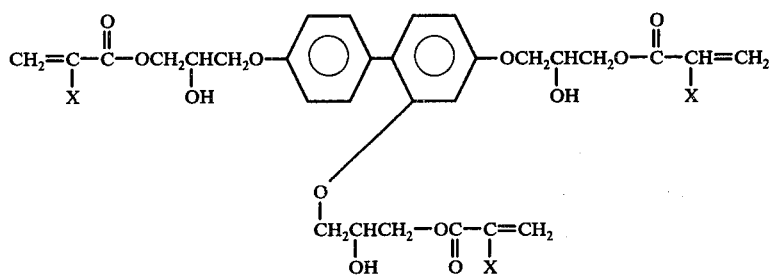

wherein X is hydrogen, lower alkyl, i.e., straight or branched chain alkyl of 1 to 4 carbon atoms, preferably methyl, or halogen, chlorine being preferred. The preferred meaning of X is methyl. A preferred example of a compound of Formula III is:

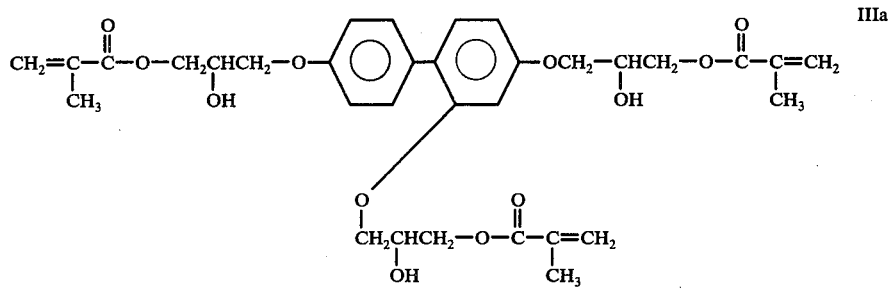

The acrylates of Formula II may be prepared by reacting BIS-GMA with an excess of an acryl chloride in the presence of a tertiary amine such as triethylamine or pyridine.

The compounds of Formula III may be prepared by reacting the triglycidyl ether of trihydroxy biphenyl with methacrylic acid in the presence of a catalyst such as a tertiary amine, triphenylphosphine, or triphenylantimony.

Also useful are compounds of the formula:

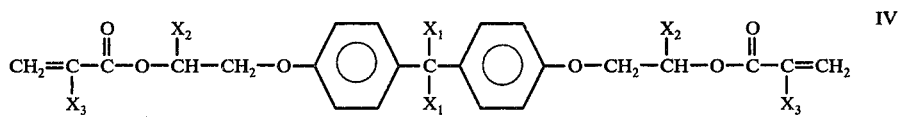

wherein $X_1$, $X_2$, and $X_3$ are either hydrogen or lower alkyl groups preferably comprising 4 or less carbon atoms. Preferred compounds of Formula IV are: bisphenol-A-bis(2-methacrylatoethyl)ether which is represented by the following formula:

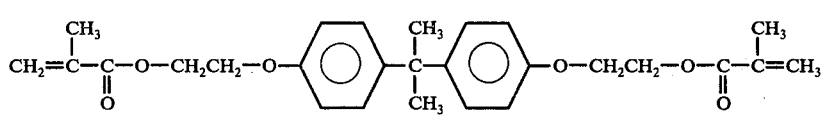

and bisphenol-F-bis(2-methacrylatopropyl)ether which is represented by the following formula:

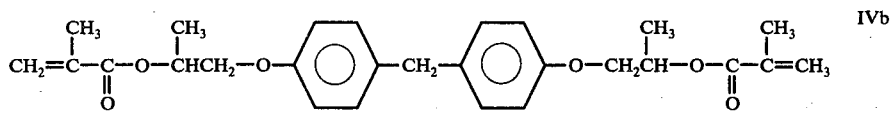

The diacrylates of Formula IV may be prepared by either of two methods. The first of these is the reaction of an acryl chloride with an appropriate bis-alcohol compound in accordance with the following reaction

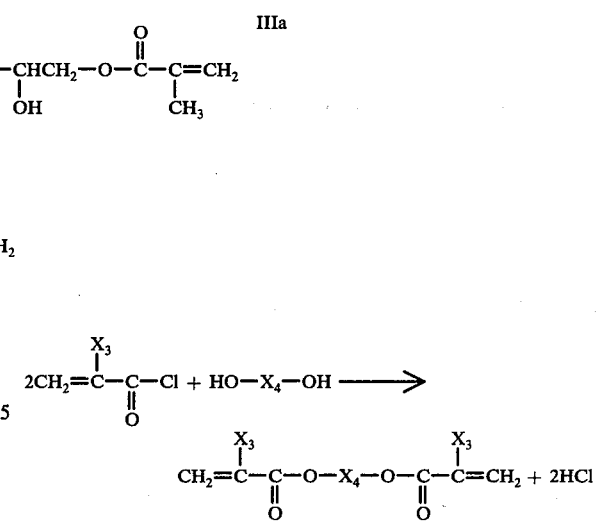

In this reaction a base may be used to remove hydrogen chloride as it forms. The base may be, for example, a tertiary amine such as triethyl amine or pyridine. On the other hand, the bis-alcohol could be pre-reacted with a base to form, for example, the disodium salt thereof which could in turn be reacted with the acid chloride.

A second method for forming the diacrylates of Formula IV is the transesterification of the appropriate bis-alcohol with lower alkyl esters of the acrylic acids in accordance with the following reaction:

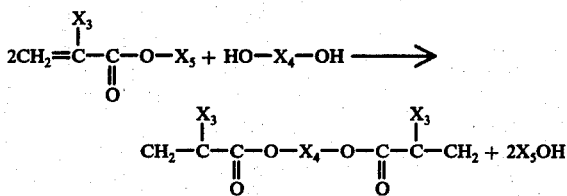

In this method any lower alkyl ester can be used; however, in practice, $X_5$ is preferably a methyl group since these methyl esters are more readily available and the product methyl alcohol is the most volatile.

Additional polyacrylates useful in the practice of this invention are compounds of the following formulae:

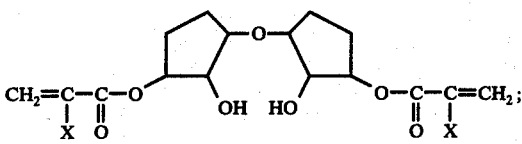

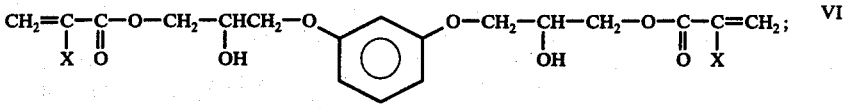

and

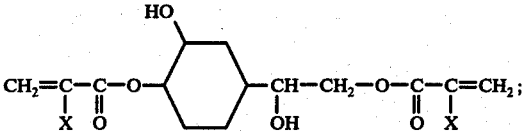

wherein in each of the formulae V–VII, X is hydrogen, lower alkyl, or halogen. In the foregoing formulae V–VII, the preferred meaning of X is methyl.

Of the compounds falling within the general formulae V–VII above which are useful in the practice of this invention, three compounds are particularly preferred. They are:

(a)

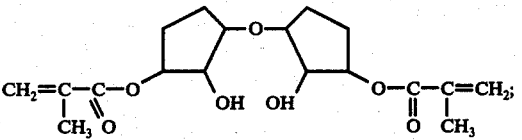

which is bis-(3-methacrylato-2-hydroxycyclopentyl)ether;

(b)

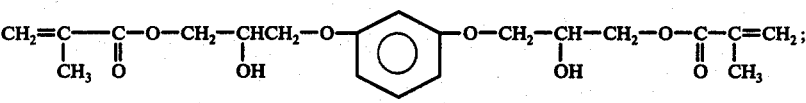

which is 1,3-bis(3-methacrylato-2-hydroxypropoxy)benzene; and (c)

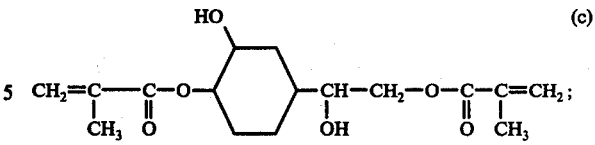

which is 1-(2-methacrylato-1-hydroxyethyl)-3-hydroxy-4-methacrylatocyclohexane.

Other representative compounds are of the formula:

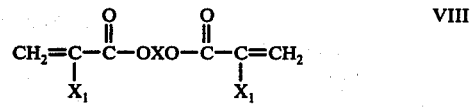

VIII wherein X is selected from

V

VI

VII

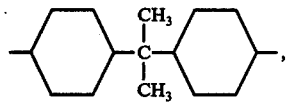 (i)

 (ii)

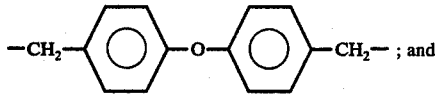 (iii)

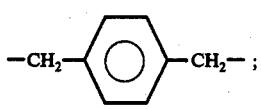 (iv)

and $X_1$ is hydrogen, lower alkyl, or halogen.

In the foregoing formula VIII, the preferred meaning of $X_1$ is methyl. X preferably is (i); thus the compound

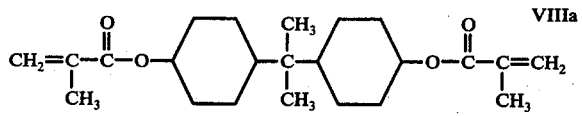

which is named 2,2-bis(4-methacrylatocyclohexyl)propane, is most preferred of those of Formula VIII.

The compounds of Formula VIII may be prepared by the reaction of an acryl chloride or derivatives thereof with the appropriate diol according to methods well known to those skilled in the art. The reaction is generally carried out in the presence of a tertiary amine such as triethylamine or pyridine as an acceptor for the hydrogen chloride generated in the reaction.

All of the compounds defined by Formula I are available commercially with the exception of the dimethacrylate or diacrylate of the diglycidyl ether of butanediol, which can be prepared readily by those skilled in the art, for example, by the reaction of an acrylic acid or methacrylic acid with the diglycidyl ether of butanediol.

Suitable catalysts and accelerators are added to the composite to provide a gel time optimally between 60 – 120 seconds, and a set time of 90 – 240 seconds. This assures that the composite will flow sufficiently to provide the necessary enamel extensions while offering a reasonable chair time in clinical practice. It is recognized, however, that under some clinical conditions slightly shorter set times may be desirable, as for example, when treating single small lesions of hypocalcified enamel, and slightly longer set times may be advantageous when treating full quadrant gingival erosion, and for these applications, formulations setting from between about 40 seconds to about 5 minutes may be required.

The catalyst and accelerator may be incorporated in separate portions of the resin which are then mixed immediately prior to application or the catalyst may be added to the filler and the dry, coated filler added to the accelerated resin just prior to application; or the catalyzed layer may be applied to the dental substrate and then coated with the accelerated layer, the mixing occuring in situ, with excess material being wiped off. The latter technique is particularly suited to the filling of developmental pits and fissures in the occlusal surfaces of adult dentition; the two-liquid system being particularly suited for the nonoperative repair of gingival erosion; and the dry filler/liquid system being particularly suited when prolonged storage life prior to application is required or when the material is to be retained without refrigeration in warmer climates.

As mentioned, the resin compositions of this invention are cured by the addition of an activator, or accelerator, and a catalyst.

The amount of accelerator depends upon the particular resin compositions which are utilized and the working time which is desired. Generally accelerators can be employed in amounts of 0.001 to 5% by weight of the monomeric resins utilized. The amount of accelerator in most cases will range from about 0.5 to 2% by weight of the monomeric resins utilized with about 1.5% generally preferred. Examples of accelerators which have been used are N,N-dimethyl-p-toluidine, para-toluene sulfinic acid, N-bis(hydroxyethyl)-p-toluidine and other tertiary amines which are well known in the art. The preferred accelerator is N-bis(hydroxyethyl)-p-toluidine.

While peroxide catalysts such as benzoyl peroxide are preferred, other catalysts well known in the art may be employed.

Catalysts are usually employed in amounts of about 0.2% to about 2% by weight of the monomeric resins. Generally amounts of about 0.50% to 1.0% by weight of the monomeric resins are satisfactory. In the instance where the catalyzed component layer is applied to the surface of the tooth before the accelerator containing component, the catalyst may be employed at higher concentrations such as about 5 to 8%.

As is well known to the art, small quantities of dyes or particulate pigments may be added to the formulation in order to achieve shades more nearly matching the natural shades of individual teeth. These, as in the case of the pigments, may be incorporated in the resinous or dry component of the composite by the manufacturer or may be supplied separately in suitable form to be added by the dentist during the final mixing process. For example, up to about 10% by weight of the resinous component of titanium dioxide may be added as an opaquing agent to mask stains in the enamel or amalgam restoratives.

The composite may also include minor amounts of common formulation ingredients used in the art such as polymerization inhibitors, for example, 25–100 ppm of hydroquinone, and U.V. stabilizers and antioxidants such as 3-tert-butyl-4-methylphenol and butylated hydroxytoluene in amounts from 0.01 to 5% by weight of the resin.

Best results are obtained where the inorganic filler is treated with a keying agent as is well recognized in the art. Such agents improve the bond between the organic polymer binder and the surfaces of the filler fibers and preserve initial strength properties in the oral environment. Keying agents which have been found highly suitable are the ethylenically unsaturated organosilane finishing or keying agents. The fiber filler may be treated with the keying agent, for example, in the manner described in U.S. Pat. No. 3,066,112 wherein an aqueous solution of tris(2-methoxyethoxy) vinyl silane is catalyzed with sodium hydroxide to give a pH of 9.3 to 9.8, and the filler treated with this solution, for example, one-half percent of the silane by weight of fused quartz. A slurry so formed is dried at about 125° C and cooled. Alternately, and preferably, the fibers are treated with a hydrolyzed neutral silane solution in dry ether as described below.

The time of the etching pretreatment depends on the particular etchant employed and the condition of the tooth. In general, the length of the pretreatment depends on the characteristic of the specific acid and the nature of the tooth. For example, a lesser exposure is normally required for deciduous and younger permanent teeth than for older permanent teeth. Teeth which have a history of fluoride may require a longer etching period than those which do not. We have found that an etch, for example, of 2 minutes with 50% phosphoric acid is generally satisfactory for adult enamel, with substantially equivalent results being obtained with a 1 minute etch of 85% phosphoric acid. The etching treatment is readily adapted to the particular situation involved by the dentist.

In order to further improve adhesion to the tooth substrate, a primer or keying agent may be applied to the tooth following the acid etch treatment. Suitable primers are the organofunctional silanes mentioned above used in treating the fiber fillers. Other keying agents well known in the art which may be employed are the reaction product of glycidyl methacrylate and N-phenyl glycine and glycerophosphoric acid dimethacrylate, among others.

Surprisingly we have found that excellent results are obtained when a silane having an epoxy functional group is employed as the primer for the composite containing the acrylate resins whereas prior teachings and experience suggest that the organofunctional group of the silanes should be of a type common to the resin component.

In the following examples, the calcium silicate fiber employed is pretreated with a silane keying agent as follows:

A mixture of 100 g of gamma-methacryloxypropyltrimethoxysilane, and 100 g of water is acidified to a pH of 3 with acetic acid and stirred at room temperature until the system becomes homogeneous. The aqueous solution is extracted with 100 g of ethyl ether, and the aqueous phase discarded. The solution contains 4.6 g of hydrolyzed silane per 100 ml of solution. Enough of the solution is added to the calcium silicate filler to place 1.2% by weight of the hydrolyzed silane on the filler. The solution is added very slowly with stirring to give good mixing. The ether solvent evaporates very quickly.

A particularly useful keying agent for priming the tooth surface to be treated is hydrolyzed gamma-glycidoxypropyltrimethoxysilane. It may be readily prepared by stirring a mixture of 200 g of 1-trimethoxysilyl-3-glycidoxypropane, and 100 g of water at room temperature until homogeneous. This solution is extracted with 500 g of ethyl ether. The aqueous phase is discarded. The ether solution contains 15.5 g of hydrolyzed silane.

The following examples describing certain representative embodiments of this invention will serve to further illustrate the nature of this invention. It is to be understood that the examples are merely illustrative, and intended to enable those skilled in the art to practice the invention in all of the embodiments flowing therefrom and do not in anyway limit the scope of the invention defined in the claims.

EXAMPLE 1

30 Parts by weight of bisphenol-A-bis(3-methacrylato-2-hydroxypropyl) ether are blended with 70 parts by weight triethyleneglycol dimethacrylate. To 100 parts of the resin blend are added 100 parts by weight of calcium silicate fibers having an average length of 5.5 microns with 97% by weight less than 20 microns, 94% by weight less than 10 microns, and diameters from 1/13 to 1/15 said length. The fibers remain suspended in the resin blend over extended periods of storage.

To 100 parts of the resin-fiber mixture are added 1.5 parts by weight N-bis(2-hydroxyethyl)-p-toluidine, 0.6 parts benzoyl peroxide, and 0.05 parts 3-tert-butyl-4-methylphenol. The composite sets in approximately 100 seconds at room temperature and hardens in about 4 minutes from the initial mixing. Physical properties of the cured composite are:

| | |
|---|---|
| Compressive Strength, psi | 18,000 |
| Diametrical Tensile Strength, psi | 3,800 |
| Hardness, Rockwell H | 91–94 |
| Solubility in H$_2$O, $\frac{gm}{cm^2 (24 \ hr.)}$ | $1.42 \times 10^{-5}$ |
| Water sorption, 24 hr., % | 2.3 |
| Shrinkage, volumetric, % | 3.3 |

A human tooth is etched for 2 minutes with a 50% solution of phosphoric acid, washed, and dried. The above composite is applied to the tooth and allowed to harden. The tooth is then submerged in water at 37° C for 24 hours. The bond strength of the composite to the enamel of the tooth is then measured as 700 psi. Examination of the sectioned tooth also shows tag-like extensions of the resin composite penetrating the enamel.

EXAMPLE 2

The teeth of a patient which exhibit areas of eroded dentin and enamel are treated with an 85% solution of phosphoric acid for 2 minutes, washed, dried and then treated with a 5% solution of hydrolyzed gamma-methacryloxypropyltrimethoxysilane.

100 Parts of the suspension of calcium silicate fibers in the resin blend described in Example 1 is divided into two equal portions of 50 parts each. 0.025 Parts of 3-tert-butyl-4-methylphenol are added to each portion. The 0.6 parts benzoyl peroxide are added to one portion and the 1.5 parts N-bis(2-hydroxyethyl)-p-toluidine added to the other portion. Equal parts of each portion are then mixed together and applied to the prepared teeth. The applied composite is allowed to harden for about 20 minutes and is then finished and polished. Examination after six months shows 100% retention and the arrest of erosion and elimination of hypersensitivity.

EXAMPLE 3

100 Parts of the calcium silicate fibers employed in Example 1 are blended with 0.6 parts benzoyl peroxide.

To 100 parts of the resin blend of Example 1 are added 0.05 parts 3-tert-butyl-4-methylphenol and 1.5 parts by weight N-bis(2-hydroxyethyl)-p-toluidine.

The occlusal surfaces of posterior teeth having developmental defects are etched for two minutes with a 50% solution of phosphoric acid, washed, and dried.

The blend of calcium silicate fibers and benzoyl peroxide is mixed with the blend of resins and other ingredients and applied to the prepared teeth. The mixture applied penetrates and fills the defects in the teeth as demonstrated by examination of sectioned teeth with a scanning electron microscope.

EXAMPLE 4

A two-component system is prepared as in Example 2, except that the component with the catalyst contains 5% by weight benzoyl peroxide and the component with the accelerator contains 1% by weight N-bis(2-hydroxyethyl)-p-toluidine.

The teeth to be treated are first etched as described in Example 2. Thereafter the component containing the benzoyl peroxide is applied to the tooth surface, spread, and then the accelerator containing component applied. The two layers interact and polymerize for a period of two minutes, after which any unreacted material is wiped away. Excellent penetration and fill of existing developmental defects is achieved as demonstrated by examination of sectioned teeth with a scanning electron microscope.

EXAMPLE 5

The teeth of a patient presenting with stained areas of teeth due to gingival erosion are treated as in Example 2 except that 5% by weight of titanium dioxide is added to the composite. The titanium dioxide presence masks the stains and generally improves the aesthetics of the restoration.

EXAMPLE 6

Example 1 is repeated, but utilizing a composite wherein the fiber filler comprises 30% by weight of the composite.

EXAMPLE 7

Example 1 is repeated, but utilizing a composite wherein the fiber filler comprises 70% by weight of the composite.

EXAMPLE 8

60 Parts by weight of bisphenol-A-bis(3-methacrylato-2-hydroxypropyl)ether and 40 parts by weight triethyleneglycol dimethacrylate are blended together and the resulting blend divided into two equal portions.

The first portion is mixed with .06% butylated hydroxytoluene, 55% calcium silicate fiber as described in Example 1, 3% 3-tert-butyl-4-methylphenol, and 0.70% benzoyl peroxide, all percentages based upon the weight of the total mixture of the portion.

The second portion is mixed with 55% calcium silicate fiber as described above, .06% butylated hydroxytoluene, 3% 3-tert-butyl-4-methylphenol, and 3% N-bis(2-hydroxyethyl)-p-toluidine, all percentages based upon weight of the total mixture of the portion.

The teeth of a patient which exhibit areas of eroded dentin and enamel are treated with a 50% phosphoric acid solution for 2 minutes, washed with water, and dried. The areas to be restored are then treated with a 5% solution of hydrolyzed gamma-methacryloxypropyltrimethoxysilane and dried.

The two fiber filler resin portions are then mixed together and the mixture applied to the prepared teeth. The composite is allowed to harden for about 20 minutes and then finished with a diamond cone and polished. Examination after six months shows 100% retention and arrest of erosion as well as the elimination of hypersensitivity caused by the erosion.

EXAMPLE 9

Example 8 is repeated, but the teeth are treated with a 10% solution of gamma-glycidoxypropyltrimethoxysilane in acetone, after etching and drying in lieu of the gamma-methacryloxypropyltrimethoxysilane. Increased bonding strengths are obtained.

As indicated above, the adhesive composite of the present invention is particularly suited for the treatment of gingivally eroded areas. The complex operative procedures previously required to effectively treat gingival erosion are eliminated. Preparation for application of the composite of the present invention requires merely that the tooth to be treated be etched with a cleanser and thoroughly dried. Priming with a keying agent, while preferred, is not necessary.

The success with the adhesive restorative composite of this invention in treating gingival erosions is illustrated by a study wherein 207 teeth in patients' mouths were treated and observed over six months. In this study, the only preparation of the teeth treated was etching with a 50% solution of phosphoric acid for approximately two minutes followed by a thorough drying of the tooth. In 202 cases the adhesive composite applied was firmly retained. In five of the teeth treated, the composite became dislodged shortly after application but reapplication following removal of precarious enamel resulted in a firm bond. The following procedure was followed in each case.

The material employed was that described in Example 8 above. Pumice only was used for prophylaxis, after which the gingival erosion was treated with a 50% phosphoric acid solution, etched for a period of about 2 minutes, the etchant being extended over all adjacent areas of the enamel. Contact of the gingival tissue by etchant produced no adverse reactions. Following the etch, the surface was washed with water prior to rinse, the surfaces isolated, and thoroughly dried with warm air. The air used for drying should be oil free. As in Example 8 above, the adhesive composite is thoroughly mixed and applied to the tooth with a polypropylene or Teflon spatula and worked to the contour and thickness desired. The material is tapered out over adjacent non-eroded enamel and gives an excellent feather edge. Finishing is accomplished after a period of about 20 minutes to avoid any possibility of the disruption of initially weak bonds. After this time, any flash is removed with diamond or whitestone and polishing performed. Margins were undetectable with an explorer.

Examination after 6 months use of the treated teeth could detect no erosion beyond the composite margins nor any ditching or marginal erosion. No contraindications for the use of the adhesive composite were observed.

Of the five cases in which the original restorations become dislodged, it is believed that these can be attributed to a presence of precarious brownish colored dentin or possible moisture contamination before the initial set.

As indicated, the adhesive composite of the present invention makes possible a conservative approach to treating gingival erosion, eliminating hypersensitivity, and greatly improving aesthetics. The composite has excellent flow characteristics which are uniquely suited to the repair of gingival erosion. It essentially can be flowed on and easily rearranged without the use of pressure. The finished margins characteristically are undetectable with an explorer, the material flowing into the tooth structure with a degree of adaptation not normally experienced with dental restoratives. Thus, the practice of this present invention permits the management of gingival erosion without the necessity of operative procedure or the sacrificing of any sound tooth structure in order to achieve retention. The adhesive restorative composite can be employed without operative technique, the pretreatment consisting merely of an acid etch, to restore demineralized tooth structure, cover stains or discoloration, restore broken edges without dulling, to repair and coat old amalgam restorations, to seal margins of prior restorations, to relieve hypersensitivity following tooth fracture, to seal various hypersensitive areas, to fill developmental defects in the posterior dentition, besides treating gingival erosions.

What is claimed is:

1. An adhesive dental restorative composite coating material to be coated over a dry tooth surface by flowing it onto the surface and that is easily rearranged on the tooth surface without pressure after application and prior to curing, comprising a suspension consisting essentially of from 40% to 70% inorganic filler fibers having a hardness on the Mohs scale of 3.5 to 6 by weight of said composite in a liquid acrylate or substituted acrylate resin composition, said resin having a viscosity of less than 5,000 centipoises, said fibers being from 1 to 100 microns in length and having (a) diameters of from 1/20 to 1/5 their said lengths, respectively, and a peroxide catalyst and an accelerator for said resin, said composite coating material being selfcuring in place to form a cured hardened coating.

2. An adhesive dental restorative composite coating material comprising a suspension consisting essentially of from 40% to 70% filler fibers of calcium silicate by weight of said composite in a liquid acrylate or substituted acrylate resin composition, said resin composition having a viscosity of less than 5,000 centipoises, said fibers being from 1 to 100 microns in length and having diameters of from 1/20 to 1/5 their lengths, respectively, and a peroxide catalyst and an accelerator for said resin.

3. An adhesive dental restorative composite coating material to be coated over a dry tooth surface that has been roughened by a conditioning treatment, by flowing it onto the surface, comprising a suspension that is easily rearranged on the tooth surface without pressure after application and prior to curing, consisting essentially of from 40% to 70% by weight of the coating material of filler fibers having a hardness on the Mohs scale of 3.5 to 6 in a liquid acrylate or substituted acrylate resin composition, said resin having a viscosity less than 5,000 centipoises, said fibers being from 1 to 100 microns in length and (a) having diameters of from 1/20 to 1/5 their said lengths respectively, said resin composition comprising from about 25% to about 90% by weight of (A) a compound of the formula:

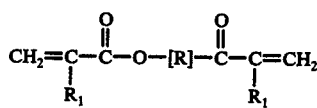

wherein
$R_1$ is hydrogen or alkyl of 1 to 4 carbons;
R is:

(a) 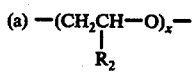

wherein x is an integer of 1 to 5, and
$R_2$ is hydrogen or an alkyl of 1 to 4 carbon atoms;
(b) — $CH_2(CH_2)_yCH_2O$ — wherein y is an integer of 1 or 2;

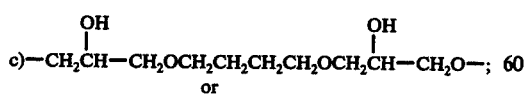
or (d) 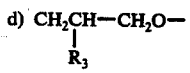

wherein $R_3$ is OH or

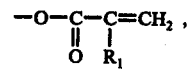

and $R_1$ has the same meaning as above;
and 10% to 75% by weight of (B), an aromatic or alicyclic polyacrylate, and small but effective amounts of a peroxide-type catalyst and of an accelerator, said coating material being self-curing in place to form a cured hardened coating.

4. A composite coating material in accordance with claim 3 wherein R is (a), $R_1$ is methyl, and $R_2$ is hydrogen.

5. A composite coating material in accordance with claim 3 wherein B is a diaromatic diacrylate.

6. A composite coating material in accordance with claim 4 wherein B is a diaromatic diacrylate.

7. A composite coating material in accordance with claim 3 wherein B is bisphenol-A-bis(3-methacrylato-2-hydroxypropyl) ether.

8. A composite coating material in accordance with claim 4 wherein B is bisphenol-A-bis(3-methacrylato-2-hydroxypropyl) ether.

9. A composite coating material in accordance with claim 4 wherein A is triethyleneglycol dimethacrylate.

10. A composite coating material in accordance with claim 8 wherein A is triethyleneglycol dimethacrylate.

11. An adhesive dental restorative composite coating material comprising a suspension consisting essentially of from 40% to 70% by weight of calcium silicate filler fibers in a liquid acrylate or substituted acrylate resin composition, said resin having a viscosity less than 5,000 centipoises, said fibers being from 1 to 100 microns in length and having diameters of from 1/20 to 1/5 their said lengths, respectively, said resin composition comprising from about 25% to about 90% by weight of (A) a compound of the formula:

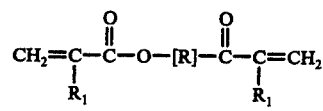

wherein
$R_1$ is hydrogen or alkyl of 1 to 4 carbons;
R is:

(a) 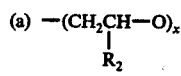

wherein x is an integer of 1 to 5, and
$R_2$ is hydrogen or an alkyl of 1 to 4 carbon atoms;
(b)—$CH_2(CH_2)_yCH_2$ O— wherein y is an integer of 1 or 2;

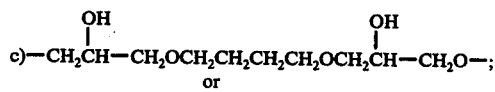
or (d) 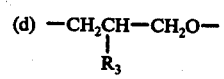

wherein
$R_3$ is OH or

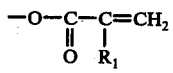

and R₁ has the same meaning as above;
and 10% to 75% by weight of (B), an aromatic or alicyclic polyacrylate, and small but effective amounts of a peroxide-type catalyst and of an accelerator, said coating material being self-curing in place to form a cured hardened coating.

12. An adhesive dental restorative composite coating material comprising a suspension consisting essentially of 40% to 70% by weight calcium silicate filler fibers in a liquid resin composition, said fibers being 1 to 100 microns in length and from 1/20 to 1/5 said length in diameter, said fibers having an average length of 5.5 microns, 97% by weight of said fibers having a length less than 20 microns, and 94% by weight of said fibers having a length less than 10 microns, said resin composition comprising from 30% to 70% by weight triethyleneglycol dimethacrylate and from 70% to 30% by weight of bisphenol-A-bis(3-methacrylato-2-hydroxypropyl) ether and having a viscosity not greater than 5,000 centipoises, and a peroxide catalyst and amine accelerator for said composition.

13. A composite coating material in accordance with claim 12 wherein said fibers comprise about 55% by weight of said composite, said resin composition comprises about 40% by weight of triethyleneglycol dimethacrylate and 60% by weight of bisphenol-A-bis(3-methacrylato-2-hydroxypropyl) ether, and said accelerator is N-bis(2-hydroxyethyl)-p-toluidine and said catalyst is benzoyl peroxide.

14. A dental restorative coating material to be coated over a dry tooth surface that has been roughened by a conditioning treatment, by flowing it onto the surface, that can be easily rearranged without the use of pressure after application and prior to curing, and that consists essentially of a flowable suspension of from 40% to 70% by weight of said suspension of filler fibers in a liquid acrylate or substituted acrylate resin composition, said resin having a viscosity of less than 5,000 centipoises, said resin comprising from about 25% to about 90% by weight of (A) a compound of the formula:

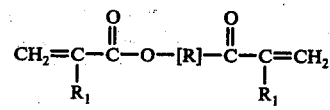

wherein
R₁ is hydrogen or alkyl of 1 to 4 carbons;
R is:

(a) 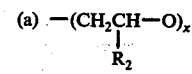

wherein $x$ is an integer of 1 to 5, and
R₂ is hydrogen or an alkyl of 1 to 4 carbon atoms;
(b) — CH₂(CH₂)ᵧCH₂O — wherein $y$ is an integer of 1 or 2;

(c) $-CH_2\overset{OH}{\underset{|}{C}}H-CH_2OCH_2CH_2CH_2CH_2OCH_2\overset{OH}{\underset{|}{C}}H-CH_2O-$; or (d) 

and
R₁ has the same meaning as above;
and 10% to 75% by weight of (B), an aromatic or alicyclic polyacrylate selected from the group consisting of

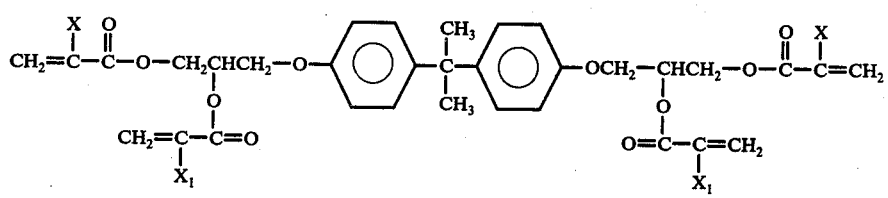

wherein each of X and X₁ may independently be hydrogen, straight or branched chain alkyl of 1 to 4 carbon atoms, or halogen:

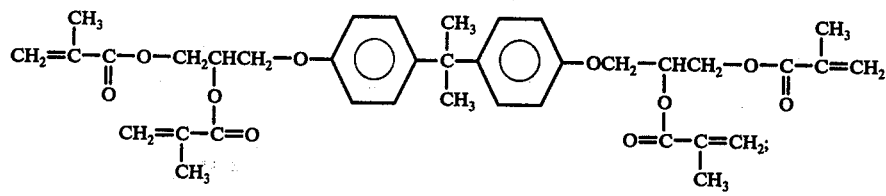

-continued

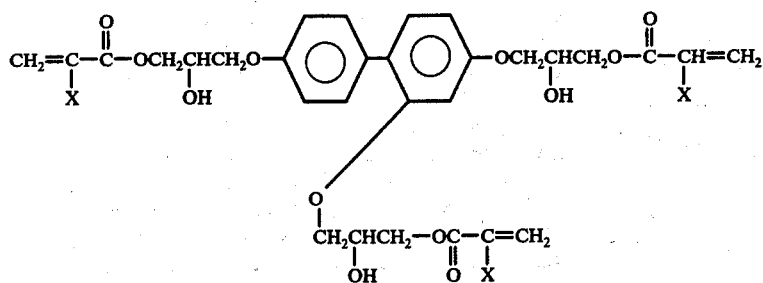

where X has the meaning above;

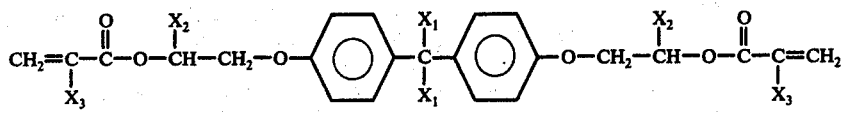

wherein $X_1$, $X_2$, and $X_3$ are either hydrogen or lower alkyl groups comprising 4 or less carbon atoms;

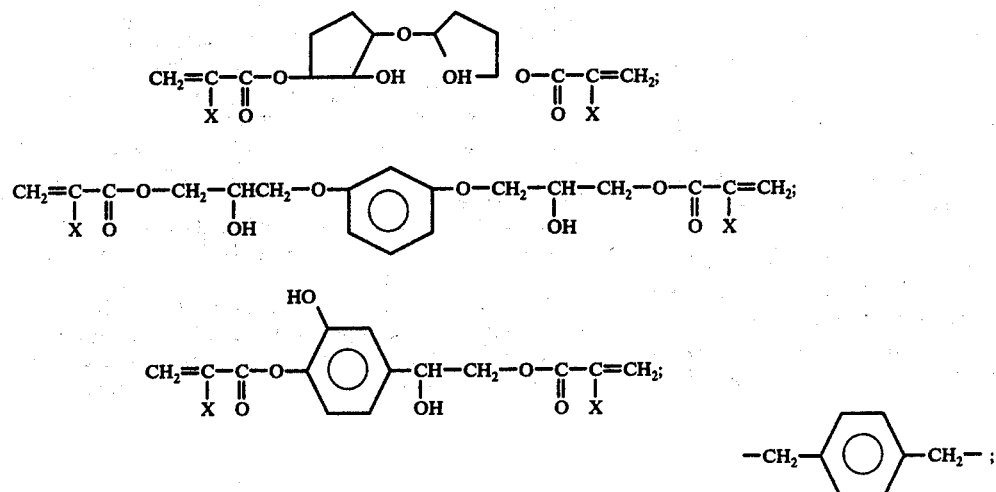

where, in the three preceding formulae, X is hydrogen, lower alkyl, or halogen;

$$CH_2=C-C-OXO-C-C=CH_2$$
$$\quad\ \ |\ \ ||\quad\quad\ \ ||\ |$$
$$\quad\ X_1\ O\quad\quad\quad\ O\ X_1$$

where X is selected from

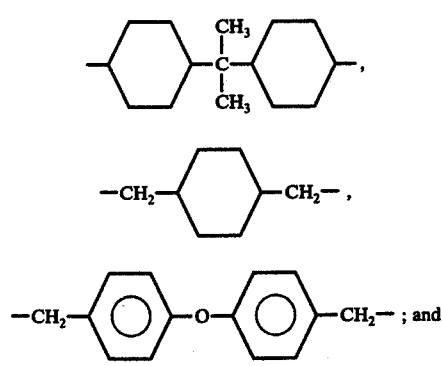

-continued $$-CH_2-\phantom{O}\bigcirc\phantom{O}-CH_2-\ ;$$

and $X_1$ is hydrogen, lower alkyl, or halogen; said fibers being from 1 to 100 microns in length and having diameters of from 1/20 to 1/5 their lengths, respectively, said coating material also containing small but effective amounts of a peroxide-type catalyst and of an accelerator, and being capable of flowing onto the roughened tooth surface to form tag-like extensions in openings in the roughened tooth surface, and being self-curing in place to form a cured, hardened coating on the tooth surface.

15. A method for repairing a defect in the surface of a tooth which comprises flowing on the tooth surface where said defect occurs an initially liquid, settable adhesive dental restorative composite as defined in claim 1 that is easily rearranged on the tooth surface without pressure after application and prior to curing, and permitting said composite to harden in situ on the tooth surface.

16. A method as claimed in claim 15 wherein a portion of said liquid resin composition and fibers containing the peroxide catalyst and free of accelerator, is applied to the tooth surface including said defect first, and the remaining portion of said liquid resin composition and fibers, with said accelerator, is then applied over said catalyst-containing portion.

17. A method of repairing a defect in the surface of a tooth which comprises flowing on the tooth surface including said defect an initially liquid, settable adhesive dental restorative composite as defined in claim 3 that is easily rearranged on the tooth surface without pressure after application and prior to curing, and permitting said composite to harden in situ on the tooth.

18. A method for repairing a defect in the surface of a tooth that comprises flowing on the tooth surface where said defect occurs an initially liquid, self-curing adhesive dental restorative composite as defined in claim 2, that is easily rearranged on the tooth surface without pressure after application and prior to curing, and then permitting the composite to harden in situ on the tooth surface.

19. A method for repairing a defect in the surface of a tooth that comprises flowing on the tooth surface where said defect occurs an initially liquid, self-curing adhesive dental restorative composite in accordance with claim 11, that is easily rearranged on the tooth surface without pressure after application and prior to curing, and permitting said composite to harden in situ on the tooth surface.

20. A method for repairing a defect in the surface of a tooth that comprises flowing on the tooth surface where the defect occurs an initially liquid, self-curing adhesive dental restorative composite in accordance with claim 12, that is easily rearranged on the tooth surface without pressure after application and prior to using, and permitting said composite to harden in situ on the tooth surface.

21. A method in accordance with claim 20, wherein said fibers comprise about 55% by weight of said composite, said resin composition comprises about 40% by weight of triethyleneglycol dimethacrylate and 60% by weight of bisphenol-A-bis(3-methacrylate-2-hydroxypropyl) ether, and said accelerator is N-bis(2-hydroxyethyl)-p-toluidine and said catalyst is benzoyl peroxide.

22. A method for repairing a defect in the surface of a tooth that comprises flowing on the tooth surface where the defect occurs an initially liquid, self-curing adhesive dental restorative composite in accordance with claim 14, and permitting said composite to harden in situ on the tooth surface.

23. A method of repairing a defect in the surface of a tooth which comprises the steps of cleaning said tooth surface with an acid cleanser, priming said cleansed tooth surface with a silane keying agent, drying said tooth surface, and flowing on said surface an initially liquid, self-curing adhesive dental restorative composite consisting essentially of a suspension of 40%–70% by weight of the suspension of calcium silicate filler fibers having average lengths of 5.5 microns, 97% by weight of said fibers having a length less than 20 microns, 94% by weight of said fibers having a length less than 10 microns, the diameters of said fibers being between 1/13 and 1/15 of the length of the fibers, in a liquid resin composition that forms the balance of the suspension and comprised of from 30% to 70% by weight triethyleneglycol dimethacrylate and from 70% to 30% by weight bisphenol-A-bis(3-methacrylate-2-hydroxypropyl) ether, said resin composition having an initial viscosity of less than 5,000 centipoise, from 0.5% to 5% by weight of a tertiary amine accelerator for said resin and from 0.2% to 8% of a catalyst for said resin, said percentages of accelerator and catalyst being based on the weight of resin, and permitting said composite to harden in situ on the tooth surface.

24. A method as claimed in claim 23 wherein said accelerator is N-bis(hydroxyethyl)-p-toluidine and said catalyst is benzoyl peroxide.

25. A method as claimed in claim 24 wherein 0.70% benzoyl peroxide is employed and about 3% of N-bis(hydroxyethyl)-p-toluidine.

26. A method as claimed in claim 24 wherein said resin composition comprises about 40% by weight triethyleneglycol dimethacrylate and about 60% by weight bisphenol-A-bis(3-methacrylato-2-hydroxypropyl) ether.

* * * * *